United States Patent [19]

Gozard et al.

[11] Patent Number: 4,775,632

[45] Date of Patent: Oct. 4, 1988

[54] ENZYMATIC TREATMENT OF SOLUTIONS OF POLYSACCHARIDE BIOPOLYMERS

[75] Inventors: Jean-Pierre Gozard, Lyons; Alain Jarry, Melle; Alain Luccioni, Bron, all of France

[73] Assignee: Rhone-Poulenc Specialites Chimiques, Courbevoie, France

[21] Appl. No.: 645,777

[22] Filed: Aug. 30, 1984

[30] Foreign Application Priority Data

Aug. 30, 1983 [FR] France ................................ 83 13885

[51] Int. Cl.⁴ ..................... C12P 19/06; C12N 9/24; E21B 43/22; C08B 37/00
[52] U.S. Cl. .................... 435/104; 435/200; 536/114; 166/246; 426/573
[58] Field of Search ............. 435/101, 104, 910, 200; 252/8.55 B; 536/1, 114, 1.1; 166/246; 426/48, 573

[56] References Cited

U.S. PATENT DOCUMENTS

| | | | |
|---|---|---|---|
| 3,966,618 | 6/1976 | Colegrove | 435/104 |
| 4,094,739 | 6/1978 | Schroeck | 435/104 |
| 4,299,825 | 11/1981 | Lee | 435/104 |
| 4,466,954 | 8/1984 | Ichikawa et al. | 424/50 |
| 4,486,330 | 12/1984 | Yoshida et al. | 252/174.12 |

FOREIGN PATENT DOCUMENTS 0049012 7/1982 European Pat. Off. .
1373487 11/1974 United Kingdom .

OTHER PUBLICATIONS

Hasegawa et al., Journal of Biological Chemistry 244(20), pp. 5460–5470 (1969).

Chemical Abstracts, vol. 77, 1972, Abstract No. 18093, "Mutanase by Fermentation", Guggenheim, Bernhard et al.

American Type Culture Collection Catalogue of Strains I, Fifteenth Edition, 1982, p. 522.

Primary Examiner—John Tarcza
Attorney, Agent, or Firm—Burns, Doane, Swecker & Mathis

[57] ABSTRACT

Aqueous solutions of polysaccharide biopolymers, e.g., Xanthomonas/carbohydrate fermentation worts, are treated with mutanase-containing enzymes to improve the filterability and injectability thereof, and are well adapted, e.g., for secondary and tertiary hydrocarbon (petroleum) recovery by waterflooding therewith.

25 Claims, No Drawings

ENZYMATIC TREATMENT OF SOLUTIONS OF POLYSACCHARIDE BIOPOLYMERS

BACKGROUND OF THE INVENTION

1. Field of the Invention

The present invention relates to the treatment of aqueous solutions of heteropolysaccharides, in particular xanthan gum, to improve the filterability and injectability thereof. This invention especially relates to the treatment of entire fermentation worts destined for the formulation of aqueous fluids adapted to displace petroleum in partially depleted deposits thereof and hence to assist in its recovery.

2. Description of the Prior Art

Heteropolysaccharides or biopolymers obtained by the fermentation of a carbohydrate under the action of bacteria of the genus Xanthomonas or Arthrobacter, or of fungi of the genus Sclerotium, are widely industrially useful because of such properties as capacity to markedly increase viscosity and to serve as thickening agents.

One of the known uses for heteropolysaccharides of xanthan gum type is in the secondary or tertiary recovery of petroleum. In this application, dilute aqueous solutions having a concentration of about 300 to 3000 ppm are used to displace the oil in partially depleted reservoirs thereof. Xanthan gum is characterized by high viscosity at low concentrations, great insensitivity to salinity and to the nature of the salts, and high stability under mechanical stress. However, solutions prepared from industrial grades, either from fermentation worts or by the dilution of a powder which has been precipitated and separated from such worts, have the major disadvantage of rapidly clogging the pores of the rock formations into which they are injected, thereby effecting undesirable rises in pressure and rapidly preventing any additional recovery of oil. It too is known that this clogging is due to the presence, on the one hand, of insoluble particles such as cellular debris and nonviable bacteria originating in the fermentation, and on the other, of a certain number of translucent aggregates or microgels, especially if the solution is prepared from biopolymers which have been precipitated from fermentation worts.

A variety of techniques have been proposed to improve the viscosity and/or the filterability and injectability of xanthan gums, including heat treatments, flocculation, enzyme treatments, etc., whether or not combined with filtration, for example, over diatomaceous earth.

In the process described in U.S. Pat. No. 3,355,447 the liquor is treated at pH 7–9, at a temperature of 65°–77° C. for at least 20 minutes, then diluted and filtered to obtain a clarified hydrophilic colloid solution.

U.S. Pat. No. 3,591,578 describes a wort treatment which involves heating the broth at a temperature of 80°–130° C. for from 10 to 120 minutes at a pH of 6.3–6.9 to increase viscosity.

U.S. Pat. No. 3,729,460 features a treatment of the solution at an alkaline pH, providing a modified structure.

In French Patent No. 2,330,697 a treatment is described: which is carried out at a temperature greater than 100° C. for from 1 to 300 minutes, the salt concentration is at least equal to 0.5% by weight and the solution is filtered. The polymer treated in a saline medium is set forth as being physically different from a polymer which has not been subjected to such a treatment.

The process described in U.S. Pat. No. 3,773,752 entails diluting the fermentation wort, addition of a coagulant and subsequent filtration, and U.S. Pat. No. 3,801,502 entails addition of an alcohol, a phenol or a nonionic surfactant over the course of the heat treatment.

According to French Patent No. 2,440,992 the salt content is less than 0.2% and the heating is carried out at 60°–98° C. for from 2 to 60 minutes.

In each of the processes immediately above described, the heat treatment is carried out either at the natural pH of the fermentation wort or at an alkaline pH.

Cf. published U.K. Patent Application GB No. 2,111,520 A, which relates to improving the clarity and filterability of xanthan gum solution by treating a crude wort at a pH of 2 to 7 with an effective amount of an acid or neutral protease and then raising the pH to 8 to 13, desirably at a temperature of from 50°–70° C. for from 0.5 to 10 hours. In Table 1, comparative Example 1(c), an inoperative experiment is described which is carried out in the absence of enzyme at a temperature of 60° C., at a pH of 5.5, for 1 hour.

In published European Patent Application No. 0,069,523 is described a process for concentrating a xanthan gum type biopolymer solution by ultrafiltration. A crude wort or solution reconstituted from powder is employed, optionally purified (albeit no details of any purification technique are set forth).

U.K. Patent Specification No. 1,488,645 (published French Patent Application No. 2,318,926) is oriented as regards increasing the viscosity of a xanthan gum wort via heat treatment at 99°–104° C., for a critical time period of from 1 to 5 minutes at a pH of 6–7. No indication of filterability characteristics is given, but, as will later be seen, a heat treatment of insufficient duration is ineffective to enhance filterability.

U.S. Pat. No. 4,299,825 relates to clarifying and concentrating a raw Xanthomonas heteropolysaccharide fermentation broth by filtration and ultrafiltration. The wort may be subjected, prior to filtration, to a heat treatment at 60°–150° C. for from 0.3 to 3 hours. The pH of the heat treatment is unspecified, thus being carried out at a natural pH of from 6.5 to 7.5. The clarified solution has a pH of 6 to 9, however, adjusted by addition of an acid or base.

Enzyme action has also been proposed to improve the injectability and filterability of aqueous solutions of xanthan gum.

U.S. Pat. Nos. 3,966,618, 4,119,491 and 4,165,257 describe treatments employing a protease type enzyme. These treatments do not permit completely overcoming the problems of clogging associated with the presence of insoluble proteinaceous substances.

And in European Patent No. 0,039,962 is described a treatment using a complex enzyme having B 1,3-glucanase and protease activity, derived from *Pellicularia filamentosa* and/or *Pellicularia sasakii*. Finally, published French Application Nos. 2,491,494 and 2,506,328 proposes an enzyme treatment utilizing polysaccharides and polysaccharase in combination with protease. It has been found that treatment solely with polysaccharase has but a limited effect. The mixed polysaccharase/-protease treatment is complicated to use, as the two types of enzyme develop their activity under different pH conditions and at different temperatures.

SUMMARY OF THE INVENTION

Accordingly, a major object of the present invention is the provision of an improved single-stage enzymatic treatment of heteropolysaccharides, to improve the injectability and filterability of dilute solutions thereof, without appreciably modifying their capacity to increase viscosity in comparison with untreated such solutions.

Briefly, the present invention features the treatment of polysaccharide solutions by enzymatic treatment and comprises contacting such solutions with an effective amount of an enzyme complex which includes mutanase.

DETAILED DESCRIPTION OF THE INVENTION

More particularly according to the present invention, the mutanases constitute a family of enzymes, the principal common feature of which is their ability to attack 1,3-glucoside bonds in the alpha position. Mutanases are produced by appropriate microorganism cultures on a medium, the principal carbon source of which is the mutane originating from Streptococcus, for example, *Streptococcus mutans* CBS No. 350-71 Microorganisms which generate mutanases include *Trichoderma harzianum, Penicillium funiculosum, Penicillium melinii* and *Penicillium janthinellum.*

The mutanase containing material that is preferably used in the process of the invention is obtained from *Trichoderma harzianum.* The culture of *Trichoderma harzianum* for the preparation of an α-1,3-glucanase (mutanase) capable of hydrolyzing an α-1,3-glucane, is described, for example, in British Patent Specification No. 1,373,487, hereby expressly incorporated by reference.

In microbial enzyme fermentations, in the absence of particularly optimum conditions, several enzyme components in relatively constant properties are typically produced. A typical such commercially available material employed in one embodiment of the invention is marketed under the trademark NOVOZYM 234 b Novo Indus tri A/S. This enzyme displays, aside from its principal mutanase activity, cellulase, laminarinase, xylanase, chitinase and proteinase activities. These multiple enzymes contribute to the results obtained by the process according to the invention.

The heteropolysaccharides used in the process of the invention are hydrophilic colloids obtained by fermentation of a carbohydrate under the action of appropriate microorganism. Exemplary such microorganisms include, for example, bacteria of the genus Xanthomonas and more particularly the species described in *Bergey's Manual of Determinative Bacteriology* (8th edition, 1974, Williams N. Wilkins Co., Baltimore), such as *Xanthomonas begoniae, Xanthomonas campestris, Xanthomonas carotae, Xanthomonas hederae, Xanthomonas incanae, Xanthomonas malvacearum, Xanthomonas papavericola, Xanthomonas phaseoli, Xanthomonas pisi, Xanthomonas vasculorum, Xanthomonas vesicatoria, Xanthomonas vitians, Xanthomonas pelargonii;* of the genus Arthrobacter and more particularly the species *Arthrobacter stabilis, Arthrobacter viscosus;* of the genus Erwinia; of the genus Azotobacter and more particularly the species *Azotobacter indicus;* of the genus Agrobacterium and more particularly the species *Agrobacterium radiobacter, Agrobacterium rhizogenes, Agrobacterium tumefaciens;* and fungi of the genus Sclerotium and more particularly the species *Sclerotium glucanicum, Sclerotium rolfii,* and the like.

Experience has demonstrated that certain species are capable of producing polysaccharides with notable efficiency. The species *Xanthomonas campestris* is especially suitable for the synthesis of xanthan gum.

A wide variety of carbohydrates may be fermented employing the microorganisms of the aforementioned genera to produce the heteropolysaccharide used in the process according to the invention. Representative carbohydrates are glucose, saccharose, fructose, maltose, lactose, starch, and the like. The fermentation of the carbohydrate is typically carried out in an aqueous medium advantageously containing up to 100 g/l of the glucide. The fermentation medium, also typically, further comprises a source of phosphorus, a source of magnesium which is an enzyme activator and a source of nitrogen which may either be of organic or inorganic, or mixed organic/inorganic in origin.

The preparation of xanthan gum is described in numerous publications and patents. Compare, for example, U.S. Pat. Nos. 3,020,206, 3,020,207, 3,391,060 and 4,154,654.

At the onset of the fermentation process and the production of the polysaccharide, the wort usually contains from about 15 to 50 g/liter of polymer, together with various constituents including bacterial cells, cellular debris, residual proteins and mineral ions.

The biopolymer may be recovered from the wort by precipitation with the aid of a precipitation agent, for example, isopropanol, followed by filtration and drying.

The process of the invention may be applied to solutions obtained by the dissolution in water of a biopolymer powder of commercial grade, but in an advantageous and preferred embodiment of the invention, destined for subsequent use in the recovery of petroleum, the entirety of the liquor from the fermentation process is used.

The enzyme comprising the mutanase is added to the aqueous solution containing from 0.15 to about 30% by weight of polysaccharide and the mixture is subjected to aging, either with or without agitation, at a temperature ranging from ambient temperature to 60° C., preferably from 25° to 55° C., for a period of time of from about 4 to 24 hours or more, at a pH of from 3.5 to 7. Advantageously, the pH is adjusted to a value of from 4 to 5.8 by the addition of an inorganic or organic acid thereto, such as sulfuric acid, phosphoric acid, nitric acid, acetic acid, formic acid, or the like.

When the solution to be treated is prepared by redissolution of a powder isolated from a fermentation wort, the polysaccharide concentration advantageously ranges from about 0.25 to 1.5% by weight.

If an entire fermentation wort is treated consistent herewith, the polysaccharide concentration advantageously ranges from about 1.5 to 20% by weight. The entire wort may itself be the product emanating directly from the fermentation, in which case the polysaccharide concentration normally ranges from 1.5 to 5% by weight, or it may be a wort that has been concentrated by conventional means to a polysaccharide concentration of up to about 20% by weight.

The amount of the enzyme complex that is added to the aqueous solution must be sufficient to insure the degradation of the insoluble polysaccharides and the bacterial cell debris.

This amount depends upon the enzymatic activity of the complex, the quantity of insoluble material in the solution to be treated and the conditions of the enzyme treatment.

When using the NOVOZYM 234 complex, an amount ranging from 0.1 to 3% by weight with respect to the weight of the xanthan gum is usually sufficient. The appropriate amount may also be calculated with respect to the nitrogen contained in the medium originating essentially from the biomass. Quantities of from 20 to 150 g, preferably from 40 to 100 g, of the enzyme per 100 g nitrogen are typically sufficient for the destruction of both the bacterial residue and the insoluble materials of other than bacterial origin.

The enzymatic treatment according to the invention is also applicable to polysaccharide solutions previously clarified by any of the known methods, such as pasteurization, centrifugation, filtration over diatomaceous earth, etc.

In a preferred embodiment of the invention, the polysaccharide solution, advantageously an entire fermentation wort, is subjected, either before or after, but preferably before the enzyme treatment, to a heat treatment at a temperature of from 60° to 150° C. for from 5 minutes to 2 hours. It has been found that the combination of a heat treatment and the enzyme treatment provides an appreciably more effective clarification of the xanthan gum solutions. Particularly favorable results in relation to viscosifying power, filterability and injectability were obtained by heat treatment of the fermentation wort at a pH ranging from 3.5 to 6.2, preferably from 4 to 5.5, at a temperature of from 60° to 110° C. and preferably from 80° to 100° C., for from 5 to 60 minutes and preferably from 15 to 30 minutes, followed by treatment with the enzyme complex.

The heteropolysaccharide solutions resulting from the subject enzyme treatment, together with the powders isolated from such solutions, are especially useful in all applications requiring clarified products, for example, in operations for the secondary and tertiary recovery of petroleum.

A dilute solution with a low concentration in polysaccharide is at a disadvantage because it cannot be transported economically. The polymer in powder form also presents problems because of the need for the redissolution thereof at the site of application. It may be advantageous in certain cases to produce a concentrated solution of the biopolymer. This concentration may be effected by conventional means, such as evaporation or ultrafiltration, with the latter method being preferred as it is more economical and permits, in a manner known per se and on an industrial scale, the separation of low molecular weight molecules from the high molecular weight molecules and concentration of the polymers without modifying their rheological properties. It has been verified in particular that ultrafiltration, even at a high velocity gradient, does not adversely affect the viscosifying power and filterabiliyy of the solutions.

Concentration by ultrafiltration may be carried out by using known methods and equipment, for example, plate, helical or tubular such apparatus. Grooved plate apparatus is preferred, wherein the polymer may be exposed to high velocity gradients of from 1,000 to 10,000 $s^{-1}$, appreciably reducing the apparent viscosity of the composition, which enables rapid transportation in large surface area industrial equipment (10–50 $m^2$ units) and an improved transfer operation. Apparatus of this type is described in published French Applications and Pat. Nos. 2,127,155, 2,141,417, 2,392,696, 2,400,380 and 2,471,507. Commercially available membranes may be used in conjunction therewith, such as cellulosic or inorganic membranes, or polymer membranes, such as polyamide, polybenzymidazole, acrylic copolymer, polyacrylonitrile, polysulfone, polyvinylidene fluoride or complex polyelectrolytes, the cutoff threshold of which varies from 10 to 100,000.

The flux is a function of temperature, pressure, speed of flow and of the viscosity and concentration of the biopolymer. It is on the order of 5 to 50 $1/hour.m^2$ for a linear velocity of 0.5 to 5 m/sec. Temperatures ranging from ambient to approximately 80° C. and pressures on the order of 1 to 15 bars, preferably 1 to 6 bars, are preferred.

Ultrafiltration normally permits obtaining concentrations of 70 to 180 g of biopolymer per kg of wort. If the enzyme complex is added prior to ultrafiltration, the enzymatic reaction continues during the polymer concentration phase.

According to another embodiment of the invention, the polysaccharide solution may be further purified by diafiltration, by adding water continuously or periodically during or after the ultrafiltration, at a rate essentially corresponding to that of the removal of the ultrafiltrate. The low molecular weight molecules resulting from the reaction of enzymatic degradation are eliminated in this manner. The product thus purified, unexpectedly, has an enhanced capacity to increase viscosity.

The treatment according to the invention may be carried out discontinuously or continuously. It either may or may not be integrated in a fermentation installation, or it may be carried out at an application site, such as in the vicinity of a petroleum well. In a preferred embodiment of the invention, the process is integrated into a composite treatment, including a heat treatment in an acid medium, enzyme treatment and concentration by ultrafiltration, with purification by continuous washing.

It has also been found that a heat treatment in an acid medium combined with the enzymatic treatment improves the performance of the ultrafiltration vis-a-vis that of a wort without heat treatment, or treated under neutral or alkaline pH conditions consonant with the prior art. In particular, with an identical pressure drop at the terminals of the ultrafilter, heat treatment in an acid medium provides more highly concentrated biopolymer solutions with higher rates of feed. It is thus possible to obtain concentrations of up to 200 and even 300 g/kg of the wort.

In another embodiment of the present invention, powder formulations containing the polysaccharide and the enzyme complex are prepared. Such formulations may contain, for example, 0.1 to 3% by weight of the enzyme and 97 to 99.9% of the polysaccharide.

These solid formulations may be directly added to the aqueous fluid to prepare the dilute solution for the intended application, with the enzymatic reaction taking place at the rate of solubilization of the polysaccharide, provided that the pH of the water of dissolution is suitably adjusted to its most effective value.

The heteropolysaccharide solutions resulting from the treatment according to the invention, together with the powders isolated from these solutions, are useful in all xanthan type gum applications, and, more specifically, in applications requiring clarified and purified products, for example, in the food and pharmaceutical industries and for purposes of the assisted recovery of petroleum.

In order to further illustrate the present invention and the advantages thereof, the following specific examples are given, it being understood that same are intended only as illustrative and in nowise limitative.

EXAMPLE 1

A fermentation wort comprising 18 g/liter of xanthan gum and obtained by carbohydrate fermentation employing *Xanthomonas campestris* was used.

A fraction of the wort was concentrated by ultrafiltration using a UFP 10 module fitted with IRIS 3038 membranes (trademarks of Rhone-Poulenc Recherches Co.) to a concentration of 112 g biopolymer per kg of wort.

A second fraction was adjusted to pH 5.5 by the addition of concentrated sulfuric acid thereto and then heated to 100° C. for 15 min. After cooling, the wort was concentrated by ultrafiltration, in a manner similar to that carried out on the first fraction, to a concentration of 112 g/kg.

To 1 kg of each of the concentrated worts, 1.1 kg of NOVOZYM 234 (trademark of Novo Industri A/S) were added. The mixture was maintained at 30° C. for 14 hours, under agitation, and then cooled to ambient temperature.

From worts treated in this manner, the viscosity of solutions having 1,000 ppm xanthan gum containing 5 g/liter NaCl was determined, together with the turbidity of the solutions at 1,000 ppm.

Viscosity measurements were taken using a Brookfield viscosimeter equipped with a UL adaptor, at 25° C., at a shear rate of 7.3 s$^{-1}$.

Turbidity was determined by measuring optical density at 650 nanometers over an optical path of 4 cm.

The results obtained are reported in the Table I which follows:

TABLE I

| | Viscosity, in mPa·s | Optical density |
|---|---|---|
| Treated with NOVOZYM 234; no heat treatment | 42.5 | 0.415 |
| Treated at 100° C./pH 5.5; then treated with NOVOZYM 234 | 63.1 | 0.144 |
| Treated at 100° C./pH 5.5; no treatment with NOVOZYM 234 (comparative example) | 59.5 | 0.749 |

EXAMPLE 2

A fermentation wort containing 80 g xanthan gum per kg of wort was continuously concentrated by ultrafiltration of a 15.6 g/kg raw wort, fractions of which were then treated at pH 5.5 for 15 min at 100° C. and other fractions were not subjected to heat treatment.

To certain 1 kg fractions of the concentrated wort, there was added 1 g of NOVOZYM 234. The mixtures were maintained at 40° C. for 14 hours, under agitation, and then cooled to ambient temperature. To another fraction, no enzyme was added.

The effect of the aforesaid treatments on filterability and injectability was determined by the tests described below, and compared with the same wort which had not been subjected to the enzyme treatment.

The results obtained are reported in the Table II which follows.

Flow or filterability test at constant flow rate

This test detects the phenomenon of clogging that may take place during the injection of a dilute biopolymer solution into a petroleum deposit and thus is a measure of the suitability of the biopolymer solution to be used in the assisted recovery of oil.

The principle of the test consists of circulating the dilute solutions at a constant flow rate through a calibrated filter. The pressure drop (ΔP) generated at the terminals of the filter by the passage of the biopolymer solution therethrough characterizes the filterability thereof.

To take into consideration the conditions of use in the field, the solutions were tested at the same viscosity (and not at the same concentration).

The tests were carried out under the following conditions:
(i) Temperature: 30° C.;
(ii) Flow rate: 22.5 ml/hour;
(iii) Millipore filters, 47 mm in diameter, pore diameters 3 μm, 8 μm and 12 μm;
(iv) Solution preparation: the wort was diluted with silane water (50 g/l NaCl and 5 g/l CaCl$_2$) such that the resulting solution had a viscosity of 35 mPa.s (measured using a Brookfield viscosimeter, with a UL adaptor at 30° C., shear rate of 7.3 s$^{-1}$; and
(v) The pressure drop, ΔP, was measured when 350 ml of the solution had been filtered. If the pressure exceeded 50 millibars, the number in parentheses indicates the volume of the filtered solution when the pressure reached 50 mb.

Injectability test at constant pressure

This test determines the injectability of dilute biopolymer solutions. The principle consists of circulating the solutions under constant pressure through a calibrated filter. The flow volume as a function of time characterizes the injectability.

The operating conditions were as follows:
(i) Millipore filters, 47 mm in diameter, pore diameters of 0.8 μm to 8 μm;
(ii) Pressure, 3 bars;
(iii) Solution preparation: identical to that of the above constant flow filterability test;
(iv) Viscosity, 35 mPa.s (Brookfield - UL adaptor, 30° C./7.3 s$^{-1}$); and
(v) The time for passage of 1,000 ml of the solution was noted. If this time exceeded 10 min, the value in parentheses indicates the solution volume filtered.

TABLE II

| Treatment 100° C./15 min pH 5.5 | Treatment NOVOZYM 234 | Filterability at constant flow rate Δp in millibars 3 μm | 8 μm | 12 μm | Injectability under 3 bars pressure Time (in min) 0.8 μm | 1.2 μm | 3 μm | 5 μm | 8 μm | Optical density 1,000 ppm solution |
|---|---|---|---|---|---|---|---|---|---|---|
| Yes | None | 50 (22.5 ml) | 44 | 6 | | | 10 min (260 ml) | 10 min (645 ml) | 1 min, 7 sec | 0.848 |
| Yes | Yes | 35 | 11.5 | 1.8 | 10 min | 9 min, | 1 min, | 32 sec | | 0.171 |

TABLE II-continued

| Treatment | | Filterability at constant flow rate Δp in millibars | | | Injectability under 3 bars pressure Time (in min) | | | | | Optical density 1,000 ppm solution |
|---|---|---|---|---|---|---|---|---|---|---|
| 100° C./15 min pH 5.5 | NOVOZYM 234 | 3 μm | 8 μm | 12 μm | 0.8 μm | 1.2 μm | 3 μm | 5 μm | 8 μm | |
| None | Yes | 50 (83 ml) | 28.4 | 3.1 | (910 ml) | 18 sec 10 min 210 ml | 21 sec 10 min (450 ml) | 10 min (740 ml) | 48 sec | 0.390 |
| None | None | clogging | | | | clogging | | | | 0.860 |

EXAMPLE 3

This example illustrates the effect of the enzyme treatment on the injectability of dilute solutions obtained from xanthan gum powders precipitated from the treated wort.

From the wort treated with the NOVOZYM 234 of Example 2, the biopolymer was isolated by precipitation with isopropanol. The fibers were washed, dried and ground.

For purposes of comparison, the biopolymer was isolated from a fraction of the same wort, but prior to the enzyme treatment.

5 g of the powder were diluted in saline water by means of a Waring blender such that the resulting solution had a viscosity of 35 mPa.s and a salt concentration of 50 g/l of NaCl and 5 g/l of $CaCl_2$.

Each of the solutions was subjected to the injectability test at constant pressure described in the preceding example. The results obtained are reported in the Table III which follows:

TABLE III

| | Injectability test at constant pressure (3 bars); Time for passage of 1,000 ml of solution at 35 mPa · s through first filters (in microns) | | | |
|---|---|---|---|---|
| | 0.8 μm | 1.2 μm | 3 μm | 5 μm |
| Fibers of an untreated wort | | 10 min (220 ml) | 10 min (905 ml) | 30 sec |
| Fibers of a wort treated with NOVOZYM 234 | 10 min (580 ml) | 1 min, 52 sec | 32 sec | 19 sec |

EXAMPLE 4

20 kg of a purified fermentation wort containing 15.6 g xanthan gum per kg of wort were heat treated for 15 min at 100° C., at pH 5.5.

To 5 kg of the wort thus treated and cooled to 40° C., 1 g of NOVOZYM 234 was added and the solution maintained at 40° C. for 10 hours. The wort was then concentrated by ultrafiltration in a UFP 2 module (trademark of Rhone-Poulenc Recherches Co.) fitted with IRIS 3038 A membranes made of acrylonitrile and having a filtering surface area of 0.022 m². The wort was concentrated to a gum content of 80 g per kg of the wort.

100 g of the wort were sampled for the constant rate injectability test.

The remaining wort was washed continuously (diafiltration) at 55° C. with deionized water by 5 times the weight of the wort in the same apparatus and reconcentrated to 80 g/kg. As a function of the washing and the final concentration, the amount of nitrogen in the retained solution decreased to reach 20% of its initial content upon completion of the operation.

The results of the injectability test at constant flow rate are reported in the Table IV which follows, and are compared with the same wort concentrated by ultrafiltration, but without heat treatment and without enzyme treatment (control).

TABLE IV

| | Solution tested | | Filterability at constant flow rate Δp in millibars | | |
|---|---|---|---|---|---|
| Nature of wort | Concentration (ppm) | Viscosity (mPa · s) | 3 μm | 8 μm | 12 μm |
| Concentrated by UF | 815 | 35 | 50 (22.5 ml) | 44 | 6 |
| Treated with NOVOZYM 234 Concentrated by UF | 815 | 35.3 | 37 | 12.1 | 1.7 |
| Treated with NOVOZYM 234 Concentrated by UF, Diafiltered | 750 | 37.2 | 35.1 | 11.4 | 1.8 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the treatment of an aqueous solution of a polysaccharide biopolymer obtained by fermentation under the action of microorganisms comprising bacteria of the genus Xanthomonas, Arthrobacter, Azotobacter, Erwinia, Agrobacterium, or fungi of the genus Sclerotium, and containing insoluble material therefrom comprising contacting such solution with an effective amount of a mutanase-containing enzyme complex sufficient to improve the filterability and injectability thereof and heat treating said aqueous solution at a temperature of from 60° to 150° C. from 5 minutes to 2 hours.

2. The process as defined by claim 1, said enzyme complex further comprising cellulase, laminarinase, xylanase, chitanase or proteinase activity or any combination thereof.

3. The process as defined by claim 1, said polysaccharide biopolymer comprising xanthan gum.

4. The process as defined by claim 3, said aqueous solution comprising from 0.15 to 30% by weight of said xanthan gum.

5. The process as defined by claim 1, said aqueous solution comprising a fermentation wort.

6. The process as defined by claim 5, said aqueous solution comprising a fermentation wort obtained by the action of Xanthomonas on carbohydrate.

7. The process as defined by claim 5, said fermentation wort having been concentrated by ultrafiltration.

8. The process as defined by claim 1, comprising aging the enzyme complex contacted aqueous solution at a temperature of from ambient to 60° C. for from about 4 to 24 hours, at a pH of from 3.5 to 7.

9. The process as defined by claim 8, comprising aging said solution at a temperature of from 25° to 55° C., at a pH of from 4 to 5.8.

10. The process as defined by claim 1, comprising heat treating said aqueous solution at a temperature of from 60° to 110° C. for from 5 to 60 minutes, at a pH of from 3.5 to 6.2.

11. The process as defined by claim 10, said temperature ranging from 80° to 100° C., said period of time ranging from 15 to 30 minutes, and said pH ranging from 4 to 5.5.

12. The process as defined by claim 1, said heat treatment being carried out prior to contacting said aqueous solution with said enzyme complex.

13. The process as defined by claim 1, said heat treatment being carried out subsequent to contacting said aqueous solution with said enzyme complex.

14. The process as defined by claim 1, comprising heat treating an aqueous solution which comprises from 0.15 to 5% by weight of the polysaccharide biopolymer at a temperature of from 60° to 110° C. for from 5 to 60 minutes, at a pH of from 3.5 to 6.2, and thence contacting said heat treated solution with said enzyme complex, at a temperature less than about 60° C.

15. The process as defined by claim 14, comprising concentrating said aqueous solution by ultrafiltration prior to contacting same with said enzyme complex.

16. The process as defined by claim 14, comprising concentrating said aqueous solution by ultrafiltration after contacting same with said enzyme complex.

17. The process as defined by claim 16, comprising purifying said concentrated ultrafiltered solution by diafiltration.

18. The process as defined by claim 1, said enzyme complex comprising from 0.1 to 3% by weight of said polysaccharide biopolymer.

19. The process as defined by claim 1, comprising purifying said enzyme complex-contacted solution by diafiltration.

20. The process as defined by claim 1, said aqueous solution further comprising a nitrogen source, and said enzyme complex being added in an amount determined by the amount of nitrogen within the biomass.

21. The product of the process as defined by claim 1.

22. The polysaccharide biopolymer powder as defined by claim 21, comprising from 97 to 99.9% by weight of said polysaccharide biopolymer and from 0.1 to 3% by weight of said enzyme complex.

23. In a hydrocarbon recovery process wherein subterranean petroleum deposits are flooded with an aqueous solution of a polysaccharide biopolymer, the improvement which comprises, utilizing as said aqueous solution therefor, a diluted solution as defined by claim 21.

24. A composition of matter comprising from 97 to 99.9% by weight of a polysaccharide biopolymer obtained by fermentation under the action of microorganisms comprising bacteria of the genus Xanthomonas, Arthrobacter, Azotobacter, Erwinia, Agrobacterium, or fungi of the genus Sclerotium and from 0.1 to 3% by weight of a mutanase-containing enzyme complex wherein the complex is principally mutanase.

25. An aqueous solution of the composition of matter as defined by claim 24.

* * * * *